United States Patent
Huang et al.

(10) Patent No.: US 7,966,708 B2
(45) Date of Patent: *Jun. 28, 2011

(54) METHOD OF CRIMPING A POLYMERIC STENT

(75) Inventors: Bin Huang, Pleasanton, CA (US); Patrick Wu, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/814,266

(22) Filed: Jun. 11, 2010

(65) Prior Publication Data
US 2010/0242254 A1  Sep. 30, 2010

Related U.S. Application Data

(63) Continuation of application No. 11/441,996, filed on May 25, 2006, now Pat. No. 7,761,968.

(51) Int. Cl.
*B23P 11/00* (2006.01)
*B23P 25/00* (2006.01)
*A61F 2/06* (2006.01)

(52) U.S. Cl. ........... 29/447; 29/557; 623/1.19; 623/1.38

(58) Field of Classification Search .................. 29/447, 29/557; 623/1.18, 1.19, 1.38
See application file for complete search history.

(56) References Cited

U.S. PATENT DOCUMENTS

| | | | |
|---|---|---|---|
| 6,080,177 A | 6/2000 | Igaki et al. | |
| 6,240,978 B1 | 6/2001 | Gianotti | |
| 6,245,103 B1 | 6/2001 | Stinson | |
| 7,622,070 B2 | 11/2009 | Atladottir et al. | |
| 7,761,968 B2 * | 7/2010 | Huang et al. ................. | 29/447 |
| 2001/0021871 A1 | 9/2001 | Stinson | |
| 2003/0083732 A1 | 5/2003 | Stinson | |
| 2004/0181271 A1 | 9/2004 | De Simone et al. | |
| 2005/0010275 A1 | 1/2005 | Sahatjian et al. | |
| 2008/0058916 A1 | 3/2008 | Huang et al. | |

* cited by examiner

*Primary Examiner* — Jermie E Cozart
(74) *Attorney, Agent, or Firm* — Squire, Sanders & Dempsey (US) LLP

(57) ABSTRACT

A method of crimping a stent to a support element is disclosed, the method comprising: positioning a polymeric stent around a support element; heating the stent, wherein the heated stent is above ambient temperature; and allowing the heated stent to radially contract onto the support element, wherein the heated stent radially contracts at least partially due to heating the stent.

20 Claims, 4 Drawing Sheets

METHOD OF CRIMPING A POLYMERIC STENT

CROSS-REFERENCE

This application is a continuation application of U.S. application Ser. No. 11/441,996, filed on May 25, 2006 now U.S. Pat. No. 7,761,968 B2, which is incorporated by reference herein.

BACKGROUND OF THE INVENTION

1. Field of the Invention

This invention relates to methods of crimping a stent onto a balloon-catheter assembly to increase retention of the stent thereon.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty. "Restenosis" refers to the reoccurrence of stenosis in a blood vessel or heart valve after it has been subjected to angioplasty or valvuloplasty.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity. Once expanded, the stent must adequately maintain its size and shape throughout its service life despite the various forces that may come to bear on it, including the cyclic loading induced by the beating heart.

A stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed to allow crimping and radially expanded to allow deployment, as described below.

Additionally, it may be desirable for a stent to be biodegradable. In many treatment applications, the presence of a stent in a body may be necessary for a limited period of time until its intended function of, for example, maintaining vascular patency and/or drug delivery is accomplished. Thus, stents are often fabricated from biodegradable, bioabsorbable, and/or bioerodable materials such that they completely erode only after the clinical need for them has ended.

In general, there are several important aspects in the mechanical behavior of polymers that affect stent design. Polymers tend to have lower strength than metals on a per unit mass basis. Polymeric struts or bar arms in a polymeric stent can crack during crimping and expansion, especially when brittle polymers are used. The portions of the stent subjected to substantial deformation tend to be the most vulnerable to failure. Furthermore, in order to have adequate mechanical strength, polymeric stents may require significantly thicker struts than required in metallic stents, which results in undesirably wider struts in polymeric stents.

Delivery and deployment of a stent are accomplished by positioning the stent about one end of a catheter, inserting the end of the catheter through the skin into a bodily lumen, advancing the catheter in the bodily lumen to a desired treatment location, inflating the stent at the treatment location, and removing the catheter from the lumen by deflating the balloon. "Delivery" refers to introducing and transporting the stent through a bodily lumen to the treated site in a vessel. "Deployment" corresponds to expanding the stent within the lumen at the treatment site. In the case of a balloon expandable stent, the stent is mounted about a balloon disposed on the catheter. Mounting the stent typically involves compressing or crimping the stent onto the balloon-catheter assembly. The stent must have sufficient retention during delivery prior to deployment of the stent at an implant site. Once the stent and catheter is positioned at an implant site, the stent is then expanded by inflating the balloon.

The balloon-catheter assembly and the attached stent must have a small delivery diameter to be able to be transported through the small diameter of the vascular system. Also, the stent must be firmly attached to the catheter to avoid detachment of the stent before it is delivered and deployed in the lumen of the patient. Detachment of the stent can result in medical complications. For example, a detached stent can act as an embolus that may create thrombosis and require surgical intervention. For this reason, stent retention on the balloon-catheter assembly is important.

What is needed is a method for crimping a polymeric stent to increase stent retention on a delivery balloon, while maintaining mechanical properties of the stent during crimping.

SUMMARY

Various embodiments of the present invention include a method for fabricating a medical assembly comprising: providing a polymeric tube fabricated from a polymer of an original inside diameter; radially expanding the polymeric tube; fabricating a stent from the radially expanded polymeric tube; positioning the stent around a support element; heating the stent, wherein the heated stent is above ambient temperature; and allowing the heated stent to radially contract onto the support element, wherein the heated stent radially contracts at least partially due to heat shrinking of the polymer of the stent, and wherein the inside diameter of the contracted stent is greater than the original inside diameter of the polymeric tube.

Further embodiments of the present invention include a method for fabricating a medical assembly comprising: providing a polymeric tube fabricated from a polymer of an original inside diameter; radially expanding the polymeric tube; fabricating a stent from the radially expanded polymeric tube; positioning the stent around a support element; heating the stent; and applying inward radial pressure on the heated stent to facilitate radial contraction of the stent, wherein the inside diameter of the contracted stent is greater than the original inside diameter of the polymeric tube.

Additional embodiments of the present invention include a method for fabricating a medical assembly comprising: providing a polymeric tube fabricated from a polymer of an original inside diameter, wherein the polymer has a glass transition temperature; radially expanding the polymeric tube; fabricating a stent from the radially expanded polymeric tube; positioning the stent around a support element; heating the stent, wherein the heated stent is above ambient temperature and at a temperature from a glass transition temperature to a melting temperature of the polymer; and allowing the heated stent to radially contract onto the support element, wherein the heated stent radially contracts at least partially due to heat shrinking of the polymer of the stent, and wherein the inside diameter of the contracted stent is greater than the original inside diameter of the polymeric tube.

DETAILED DESCRIPTION

For the purposes of the present invention, the following terms and definitions apply:

The "glass transition temperature," Tg, of a polymer is the temperature at which the polymer's amorphous domains transform from a brittle vitreous state to a solid deformable or ductile state at atmospheric pressure. In other words, Tg corresponds to the temperature where segmental motion starts in the polymer chains. When an amorphous or semicrystalline polymer is exposed to an increasing temperature, both the polymer's coefficient of expansion and heat capacity increase as the temperature is raised, indicating increased molecular motion. As the temperature is raised, the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

"Use" of a stent includes manufacturing, assembling (e.g., crimping a stent on balloon), delivery of a stent through a bodily lumen to a treatment site, deployment of a stent at a treatment site, and treatment of a deployed stent. Both a scaffolding or substrate and a coating on a scaffolding experience stress. For example, during deployment, the scaffolding and/or coating of a stent can be exposed to stress caused by the radial expansion of the stent body. In addition, the scaffolding and/or coating may be exposed to stress when it is mounted on a catheter from crimping or compression of the stent. These stresses can cause the scaffolding and/or coating to fracture and the coating to tear and/or detach from the scaffolding. Failure of the mechanical integrity of the stent while the stent is in a patient can lead to serious consequences. For example, there is a risk of embolization caused by pieces of the polymeric scaffolding and/or coating breaking off from the stent.

Figure 1:
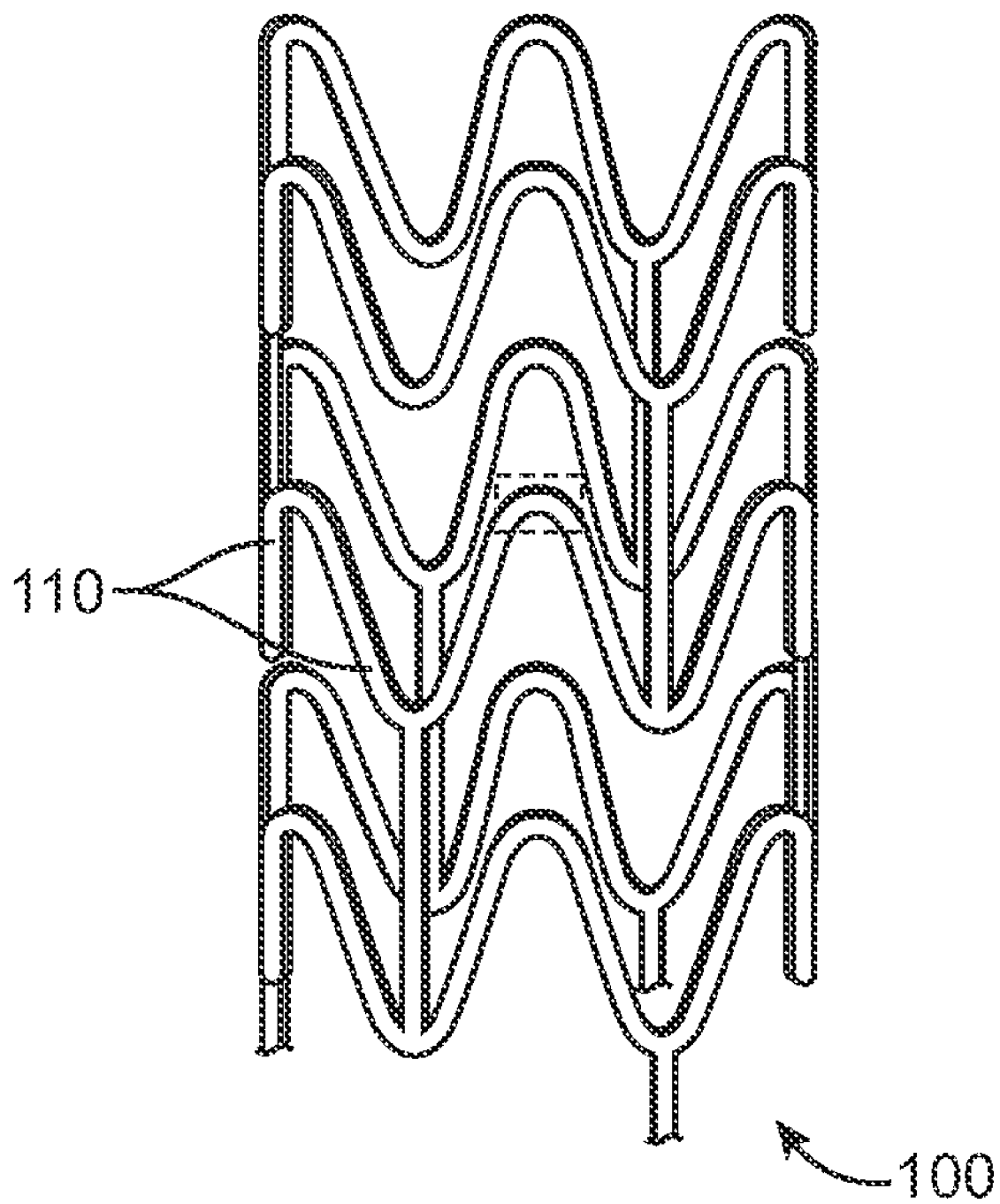
FIG. 1 depicts a stent.

FIG. 1 depicts an example of a three-dimensional view of a stent 100. Stent 100 includes a pattern with a number of interconnecting structural elements or struts 110. The embodiments disclosed herein are not limited to stents or to the stent pattern illustrated in FIG. 1, as other stents and patterns are possible. A pattern can be formed on a tube by, for example, laser cutting a pattern on the tube.

Figure 2:
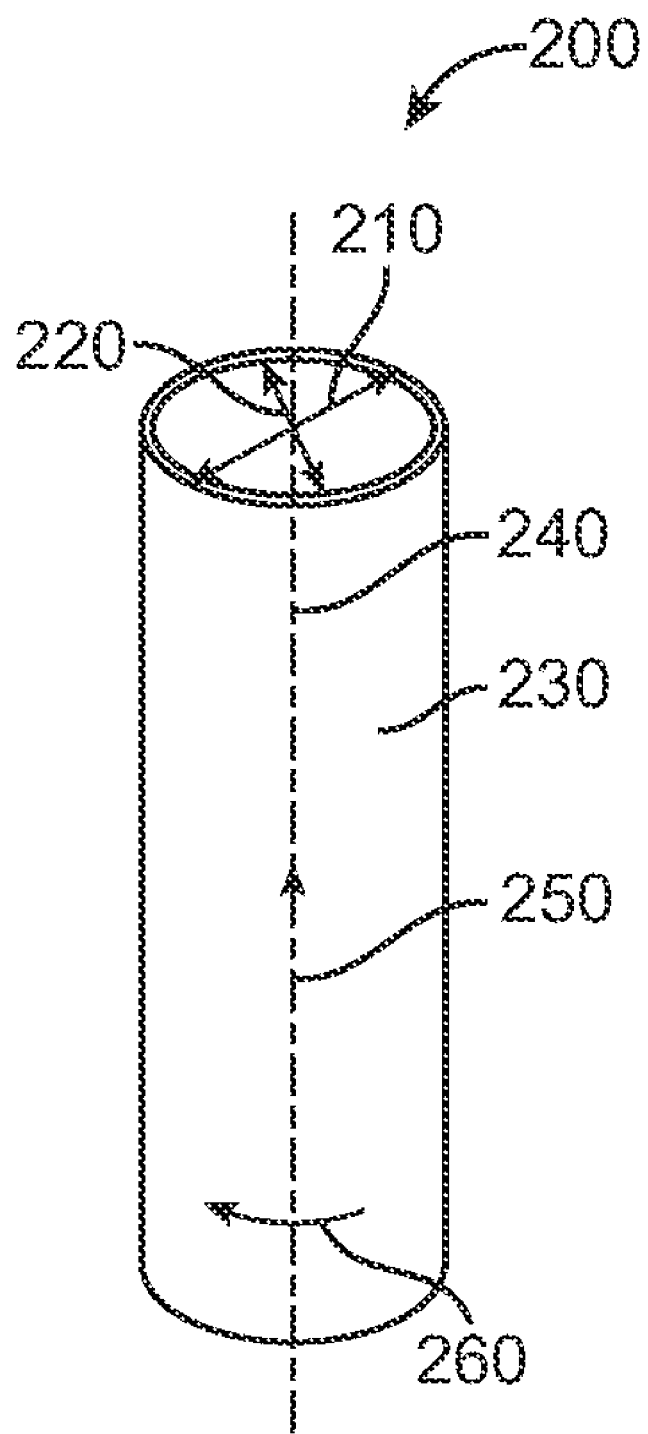
FIG. 2 depicts a polymeric tube.

A stent may be fabricated from a polymeric conduit or tube, such as polymeric tube 200 depicted in FIG. 2. Polymeric tube 200 may be cylindrical or substantially cylindrical in shape. Polymeric tube 200 has an outside diameter 210 and an inside diameter 220. Tube 200 has a surface 230 and a cylindrical axis 240.

In general, a stent can be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Additionally, a stent should also have adequate strength along the axial direction. Therefore, it is desirable to fabricate a stent from polymeric tube 200 with adequate strength in the axial direction, as shown by an arrow 250 and in the circumferential direction as indicated by an arrow 260. A stent fabricated from a tube with biaxial molecular orientation, in other words, a tube with a desired degree of polymer chain alignment in both the axial and the circumferential directions, exhibits better mechanical behavior during use of the stent.

Stent retention on the balloon-catheter assembly be difficult for polymeric stents. One reason for stent retention being more difficult in polymeric stents is that polymeric stents may require relatively wider struts than metal stents to achieve required mechanical properties. Wider struts in polymeric stents result in smaller gaps between struts, providing less space for the balloon to protrude through when the stent is crimped onto the balloon. Protrusion of the balloon through stent gaps greatly facilitates stent retention. The reduced stent retention due to wider struts in polymer stents increases the likelihood of detachment of the stent or premature deployment of a stent in the body Furthermore, the polymeric delivery balloon is often heated during crimping to enhance or facilitate protrusion of the balloon through gaps between stent struts. However, Tg of the balloon can be similar to Tg of the stent. Since heating the balloon also heats the stent, the stent becomes more flexible which further reduces protrusion of the balloon through stent struts.

As is known by those of skill in the art, applying stress to deform a polymeric material can increase the strength of the material along the direction of stress. The induced strength arises from alignment of polymer chains along the direction of stress. Thus, radial strength in a polymeric tube can be induced by radially expanding a polymeric tube. Additionally, axial strength can be induced by axially deforming a tube. The increased strength allows fabrication of a stent with thinner struts which enhances protrusion of a balloon through struts during crimping. Various embodiments of a method can include fabricating a stent from a radially expanded tube.

Various embodiments of methods to fabricate stents and stent-balloon assemblies are described herein. In some embodiments, a stent is crimped onto a delivery balloon to form a stent-balloon assembly by heat setting a stent made from a radially expanded tube. Generally, the inside surface of a stent may be positioned adjacent the outside surface of the delivery balloon and allowed to heat set onto the outside surface of the delivery balloon.

When a polymer is heated, the polymer tends to shrink from a deformed state to an originally deformed state. In the case of a stent fabricated from a radially expanded tube, heating the stent can cause the stent to shrink from the expanded diameter towards the original or deformed diameter.

Therefore, a stent may be crimped by heating the stent to a temperature above ambient temperature. In an embodiment, heating the stent allows the stent to heat shrink onto the outer surface of the delivery balloon. In one embodiment, the stent may be crimped onto the balloon with no substantially inward radial force on the stent. In another embodiment, the stent may be crimped both with heat shrinking and inward radial pressure.

However, heating the stent can reduce or dissipate the induced molecular orientation from radial expansion. Thus, there is concomitant loss or dissipation of induced strength due to loss in orientation. The embodiments of the invention include fabricating a stent such that a selected degree of residual induced orientation and strength in the stent remains even after heat shrinking or crimping the stent onto the balloon.

The invention provides methods for crimping a stent to a delivery balloon. In some embodiments, a method includes radially expanding a polymeric tube of an original inside diameter to an expanded inside diameter. In an embodiment, the method also includes positioning the stent around a delivery balloon and heating the stent to a temperature above ambient temperature. By heating the stent to a temperature above ambient temperature, the stent heat shrinks onto the delivery balloon, conforming to the outer surface of the balloon to the stent.

Figure 3A:
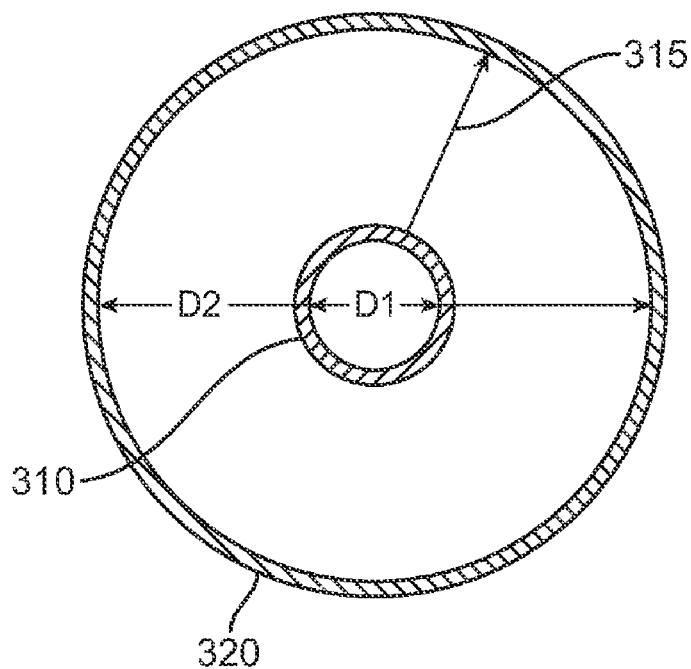
FIG. 3(a) depicts a polymeric tube that is radially expanded from an original inside diameter to a radially expanded inside diameter.
Figure 3B:
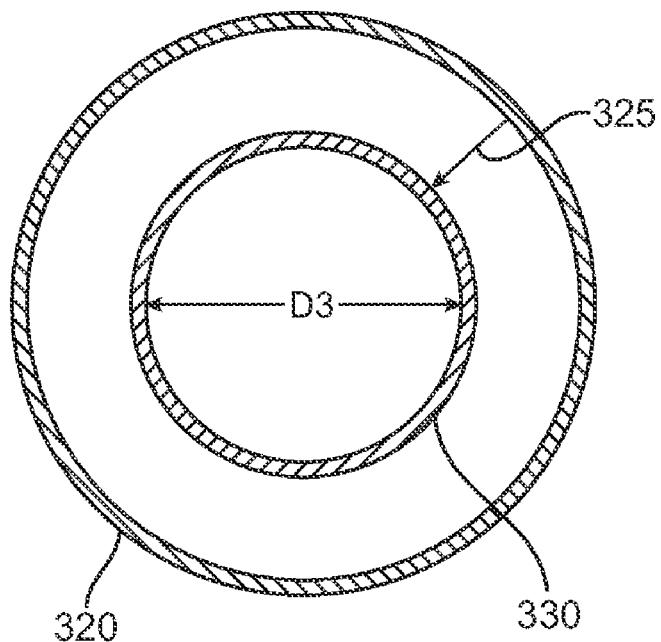
FIG. 3(b) depicts a stent fabricated from the polymeric tube that heat shrinks from a radially expanded diameter.

FIG. 3(a) depicts a polymeric tube 310 radially expanded from an original inside diameter D1 to a radially expanded inside diameter D2. As depicted, a polymeric tube 310 has an initial inside diameter D1. Polymeric tube 310 having initial inside diameter D1 is formed by any means, such as blow molding. Polymeric tube 310 is radially expanded, as indicated by arrow 315, to a radially expanded polymeric tube 320 having radially expanded inside diameter D2. After expanding the polymeric tube, a stent may be fabricated from the radially expanded polymeric tube 320 using methods known to those of skill in the art, including forming a pattern in the polymeric tube, such as with a laser. Once the stent is fabricated, the stent may then be positioned around a delivery balloon. As depicted in FIG. 3(b), the stent is heated to a temperature above ambient temperature and allowed to heat shrink from expanded stent 320 to a heat shrunk stent 330, as indicated by an arrow 325, having diameter D3.

In some embodiments, the polymeric tube from which the stent is fabricated has an original inside diameter that is less than the outside diameter of the delivery balloon. The polymeric tube with an original inside diameter is smaller than the delivery balloon. In this way, when the stent fabricated from the radially expanded tube is allowed to heat shrink to the balloon diameter, there is adequate residual radial orientation and thus residual induced strength at the crimped diameter.

In one embodiment, the polymeric tube that is later radially expanded has an original inside diameter of from about 0.001 to 0.05, or more narrowly, 0.008 to 0.01 inches. As known by those skilled in the art, a polymeric tube is formed by means of various types of methods, including, but not limited to extrusion, blow molding, or injection molding. The polymeric tube may also be formed from sheets or films that are rolled and bonded.

The degree of radial expansion may be quantified by a blow-up ratio: Outside Diameter of Deformed Tube/Original Inside Diameter of Tube. From the blow up ratio, a percent radial expansion can be determined.

(Blow up ratio−1)*100=% Radial Expansion

The polymeric tube may be radially expanded to an inside diameter greater than the size of an outside diameter of the delivery balloon. For example, the polymeric tube may be radially expanded to an inside diameter 25% to 50% greater than the outside diameter of the balloon. In some embodiments, the polymeric tube is expanded radially at least 300%, 400%, 600%, or at least 900%. By radially expanding the polymeric tube to a diameter greater than the outside diameter of the delivery balloon, adequate residual radial expansion remains after heat shrinking the stent onto the delivery balloon. In one embodiment, the inside diameter of the radially expanded polymeric tube is from about 0.060 inches to about 0.070 inches.

In some embodiments, a stent is fabricated from the radially expanded tube. The inner surface of the stent may then be positioned over the outer surface of the balloon and allowed to heat shrink onto the balloon so to conform to the outer surface of the balloon. After heat shrinking, sufficient residual radial expansion of the stent is maintained as required by the stent. For example, at least 200%, 300%, or at least 400% residual expansion of the heat shrunk stent may be maintained in the stent as compared to the original inside diameter of the polymeric tube. Residual expansion is the amount of radial expansion or orientation remaining in the stent after heat shrinking as compared to the original inside diameter of the polymeric tube. Residual expansion depends on the diameter of the original polymeric tube, the degree of radial expansion of the polymeric tube, as well as the degree that the stent formed of the polymeric tube is heat shrunk after heating the radially expanded stent. The degree that the stent heat shrinks after heating the stent depends on the diameter of the balloon, as the balloon acts to limit further heat shrinking when the inside diameter of the stent reaches the outside diameter of the balloon. The residual percent expansion is defined as follows:

(diameter of heat shrunk stent/original diameter of tube before expansion−1)*100=% Residual Radial Expansion As mentioned previously, the diameter of the stent after heat shrinking depends on the diameter of the balloon because the stent heat shrinks onto the balloon upon heating. Therefore, upon increasing a balloon's diameter, a tube with a larger original diameter before expansion can be used to arrive at a same % residual radial expansion. One advantage of starting with a larger original diameter tube is that it may be easier to manufacture than smaller diameter tubes, such as with conventional blow molding processes.

Alternatively, if a balloon with a larger diameter is used, and the size of the original polymeric tube is the same, the same residual radial expansion can be achieved even though the original polymeric tube is expanded to a lesser degree, because the expanded tube heat shrinks to a lesser degree while maintaining a certain percent radial expansion.

In one embodiment, the outside diameter of the balloon is increased to reduce the degree that the stent heat shrinks to arrive at the outer surface of the balloon. In this way, the loss of radial expansion in the process of heat shrinking is reduced. The extent that the stent is required to heat shrink and conform to the size of the outside diameter of the balloon is reduced. For example, rather than an inside diameter of the balloon of 0.033 inches, the outside diameter of the balloon can be, for example, 0.040 inches. In this way, the stent positioned over the larger diameter balloon heat shrinks less to conform to a larger diameter of the balloon, and less radial expansion is lost during heat shrinking. The size of the balloon can be of any size that allows delivery into a selected lumen.

Figure 4A:
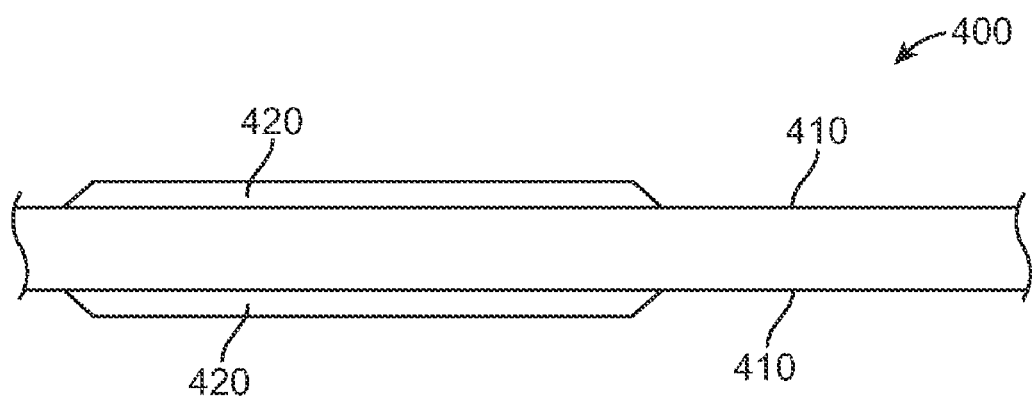
FIG. 4(a) depicts a side view of balloon-catheter assembly.

FIG. 4(a) depicts a side view of a balloon-catheter assembly 400. Balloon-catheter assembly 400 includes a balloon 420 attached to a catheter 410.

Figure 4B:
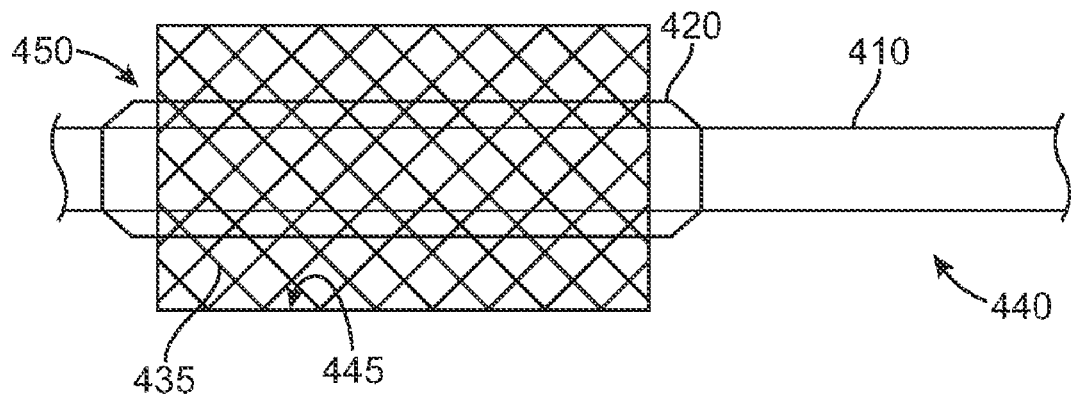
FIG. 4(b) depicts a side view of a radially expanded stent that is positioned adjacent the balloon.

FIG. 4(b) depicts a side view of a stent 435 fabricated from an expanded tube positioned over balloon 420 to form a medical assembly 440. To heat shrink the stent 435 onto a delivery balloon 420, inner surface 445 of stent 435 may be positioned adjacent an outer surface 450 of delivery balloon 420 and heated. Stent 435 may be heated for about one minute to about two hours, more narrowly, between about two minutes to about ten minutes, or more narrowly, between 30 seconds to about 1 minute. Upon heating stent 435, stent 435 heat shrinks to form heat shrunk stent 445 that conforms to surface 450 of balloon 420, thereby increasing stent retention on the balloon.

Several ways to heat the radially expanded stent and cause heat shrinking onto the balloon may be used in the invention. For example, a heated gas may be blown on the stent. Also, the stent and the balloon may be placed within or around a heated mold. Further, the stent and the balloon may be placed in an oven. Still further, the stent may be heated with a heated crimper.

The stent may be heated to a temperature above ambient temperature. Also, the temperature may be between about Tg to the melting temperature (Tm) of the polymer of the stent. Further, the temperature may be between about Tg to about Tg+50° C. The temperature of the stent may be increased gradually or rapidly. The temperature of the stent may be increased and then maintained at a certain temperature. The temperature of the stent may also be increased then decreased. In one embodiment, heat may be applied to the stent while applying inward radial pressure before, after, and/or during the time that the stent is heated.

Figure 4C:
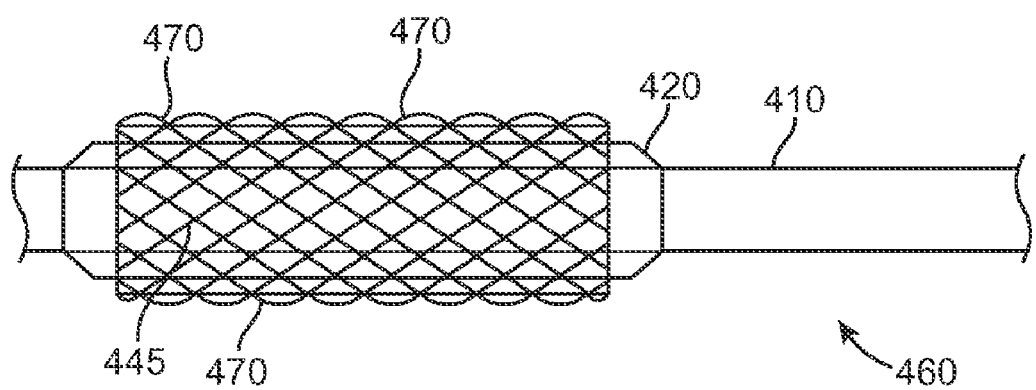
FIG. 4(c) depicts a side view of a stent that has been allowed to heat shrink onto the balloon.

FIG. 4(c) depicts a side view of a heat shrunk stent 445 on balloon 420, forming a medical assembly 460. To form medical assembly 460, inner surface 445 of stent 435 may be positioned adjacent the outer surface 450 of balloon 420 while stent 435 is in an expanded state. Stent 430 may be heated before, during, or after being positioned around balloon 420. Stent 430 then "heat shrinks" or decreases in diameter and conforms to the surface of balloon 420. In one embodiment, heat applied to medical assembly 460 facilitates balloon protrusion 470 through stent 445. Heat shrunk stent 445 conforms to outer surface 450 of balloon 420. Protrusions 470 of balloon 420 through stent 430 increase stent retention on balloon 420. Higher retention thus may be achieved by increasing the number and/or size of protrusions 470 of balloon 420 through stent 430.

Without being limited by theory, it is believed that during "heat shrinking," the radial orientation or alignment of polymer chains in heat shrunk stent 445 are reduced due to relaxation of the polymer chains. Because the molecular orientation in the stent is relaxed during heat shrinking, mechanical properties are also modified during heat shrinking. The degree of reduction in polymer chain alignment depends on the temperature of the stent. For example, below the glass transition temperature of a polymer, polymer segments may not have sufficient energy to move past one another. In general, relaxation of polymer chain alignment during heat shrinking may not be induced without sufficient segmental mobility. Above Tg, heat shrinking and relaxation may be readily induced since rotation of polymer chains, and hence segmental mobility, is possible. Between Tg and Tm of the polymer, rotational barriers exist, however, the barriers are not great enough to substantially prevent segmental mobility. As the temperature of a polymer is increased above Tg, the energy barriers to rotation decrease and segmental mobility of polymer chains tend to increase. As a result, as the temperature increases above Tg, heat shrinking and polymer chain relaxation are more easily induced.

Increasing the temperature of the stent causes heat shrinking of the stent and results in reduction of circumferential polymer chain alignment and modification of the mechanical properties of the polymer in the stent. In one embodiment, the stent is heated to a temperature above the Tg of the polymer. As the temperature increases above Tg, segmental mobility increases, which allows increase in relaxation of polymer chains. Consequently, the amount of shrinking depends on the temperature of a polymeric material.

In one embodiment, the temperature of the stent may be maintained at greater than or equal to Tg of the polymer and less than or equal to Tm of the polymer for a selected period to time. In other embodiments, the temperature of the stent is maintained at greater than or equal to Tg of the polymer and less than or equal to Tg+30° C.

In addition to the temperature, another variable to the degree of heat shrinking in the stent is the percent radial expansion of the polymer tube. In one embodiment, as previously mentioned, the polymeric tube used to fabricate the stent is radially expanded from an original inside diameter of the polymeric tube to at least 400%, at least 500%, at least 600%, or at least 900% radial expansion. In this way, heat shrinking the stent onto the balloon allows the stent to have residual radial expansion that is required of the stent during use. Although the percent radial expansion and circumferential orientation of polymer chains are decreased in the heat shrinking process, a residual radial expansion of at least 200%, 300%, or at least 400% is maintained on the stent that has been allowed to heat shrink. Although some radial expansion and polymer chain orientation is lost during heat shrinking, the residual radial expansion and radial strength in the stent is maintained. Additionally, retention of the stent on the balloon is increased due to balloon protrusions 440 through stent 430. Thus, stent retention on the balloon 420 is increased, while adequate radial expansion is maintained.

It may be advantageous to reduce heat quickly or quench the stent after heat shrinking to reduce the loss of alignment in the stent, since loss of alignment is a time dependent process. In one embodiment, the stent is cooled to a temperature below Tg after the stent heat shrinks onto the balloon. Cooling the stent to a temperature below Tg may facilitate maintaining the stent's proper shape, size, and length following the heat shrinking. Upon cooling, the stent retains the length and shape imposed by the outer surface of the balloon.

As indicated above, a stent can be formed from a tube or a sheet rolled into a tube. A sheet or tube, for example, may be formed by various methods known in the art such as extrusion or injection molding. A pattern may then be formed in the polymeric tube by laser cutting or chemical etching.

Additionally, as indicated above, a stent fabricated from embodiments of the stent described herein can be medicated with an active agent. A medicated stent may be fabricated by coating the surface of the polymeric scaffolding with a polymeric carrier that includes an active or bioactive agent or drug. An active agent or drug can also be incorporated into the polymeric scaffolding made from the blend.

Embodiments of the method described herein may be applied to balloon expandable stents, self-expanding stents, stent grafts, and stent-grafts. In the case of a self-expanding stent, the stent can be crimped over a support, such as a catheter. The stent is used to open a lumen within an organ in a mammal, maintain lumen patency, or reduce the likelihood of narrowing of a lumen. Examples of such organs include, but are not limited to, vascular organs such as, for example, coronary arteries or hepatic veins; renal organs such as, for example, urethras and ureters; biliary organs such as, for example, biliary ducts; pulmonary organs such as, for example, tracheas, bronchi and bronchioles; and gastrointestinal organs such as, for example, esophagi and colons.

A stent may be configured to degrade after implantation by fabricating the stent either partially or completely from biodegradable polymers. Polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and may be gradually absorbed and eliminated by the body.

A biodegradable stent may remain in the body until its intended function of, for example, maintaining vascular patency and/or drug delivery is accomplished. For biodegradable polymers used in coating applications, after the process of degradation, erosion, absorption has been completed, no polymer will remain on the stent. In some embodiments, very negligible traces or residue may be left behind. The duration is typically in the range of six to twelve months, although other durations are possible.

Biodegradation refers generally to changes in physical and chemical properties that occur in a polymer upon exposure to bodily fluids as in a vascular environment. The changes in properties may include a decrease in molecular weight, deterioration of mechanical properties, and decrease in mass due to erosion or absorption. Mechanical properties may correspond to strength and modulus of the polymer. Deterioration of the mechanical properties of the polymer decreases the ability of a stent, for example, to provide mechanical support in a vessel.

Representative examples of polymers that may be used to fabricate a stent coating include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(L-lactide-co-ε-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating a stent according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol. The stents may also be metallic; low-ferromagnetic; non-ferromagnetic; biostable polymeric; biodegradable polymeric or biodegradable metallic.

Some embodiments of the present invention are illustrated by the following Examples. The Examples are being given by way of illustration only and not by way of limitation.

EXAMPLES

Example 1

Polymeric tube of poly(L-lactide) (PLLA) was extruded to an inside diameter of 0.008 in. Polymeric tube was expanded to an inside diameter of 0.06 in. Patterns were then cut into the tube to fabricate a stent. The stent was positioned around a balloon-catheter assembly, where the outer diameter of balloon was 0.03 inches. Stent and balloon-catheter assembly was then heated to 100° C. for 1 minute with a heated crimper. The stent was allowed to heat shrink to the outer diameter of the balloon. Heat shrunk stent had a residual radial expansion of 200%.

Example 2

Polymeric tube of poly(L-lactide) was extruded to an inside diameter of 0.008 in. Polymeric tube was then expanded to an inside diameter of 0.06. Patterns were then cut into the tube to fabricate a stent. The stent was positioned around a balloon-catheter assembly. Outer diameter of balloon was 0.04 inches. Stent and balloon-catheter assembly was then heated to 100° C. with a heated crimper. Heat shrunken stent had a radial expansion of 200%.

This invention has been described in relation to certain examples of its application, such as its applicability to stents made up of semi-crystalline PLLA. The examples are not intended nor should they be construed as limiting this invention in any manner. Those skilled in the art will recognize, based on the disclosures herein, other polymers and other stents to which the invention herein may be applied. All such polymers and stents are within the scope of this invention.

The invention claimed is:
1. A method for fabricating a medical assembly comprising:
   providing a polymeric tube fabricated from a polymer of an original inside diameter;
   radially expanding the polymeric tube;
   fabricating a stent from the radially expanded polymeric tube;
   positioning the stent around a support element;
   heating the stent, wherein the heated stent is above ambient temperature; and
   allowing the heated stent to radially contract onto the support element, wherein the heated stent radially contracts at least partially due to heat shrinking of the polymer of the stent, and wherein the inside diameter of the contracted stent is greater than the original inside diameter of the polymeric tube.
2. The method according to claim 1, wherein the polymer is poly(L-lactide).

3. The method according to claim 1, wherein the support element is a delivery balloon.

4. The method according to claim 1, wherein the support element is a catheter.

5. The method according to claim 1, wherein the polymeric tube is radially expanded to an inside diameter greater than the outside diameter of the support element.

6. The method according to claim 1, wherein the polymeric tube is radially expanded to an inside diameter 25% to 50% greater than the outside diameter of the support element.

7. The method according to claim 1, wherein a percent radial expansion of the radially expanded polymeric tube is from about 400% to about 900% as compared to the original inside diameter of the tube.

8. The method according to claim 1, wherein the stent is heated to a temperature of about glass transition temperature to about glass transition temperature +50° C. of the polymer in the stent.

9. The method according to claim 1, wherein the heated stent is allowed to radially contract to a size of about an outside diameter of the support element.

10. The method according to claim 1, wherein the contracted stent has a radial expansion of about 200% to about 400% as compared to the original inside diameter of the polymeric tube.

11. The method according to claim 1, wherein the support element has an outside diameter of about 0.040, and the stent heat shrinks to an inside diameter of about 0.040.

12. The method according to claim 1, wherein the polymer comprises a bioabsorbable polymer.

13. The method according to claim 1, wherein fabricating a stent from the radially expanded tube comprises forming a pattern on the radially expanded tube including a plurality of struts.

14. The method according to claim 1, further comprising applying inward radial pressure on the stent to facilitate the radial contraction of the stent.

15. The method according to claim 1, wherein the stent radially contracts onto the support element with no inward radial force on the stent.

16. A method for fabricating a medical assembly comprising:
    providing a polymeric tube fabricated from a polymer of an original inside diameter;
    radially expanding the polymeric tube;
    fabricating a stent from the radially expanded polymeric tube;
    positioning the stent around a support element;
    heating the stent; and
    applying inward radial pressure on the heated stent to facilitate radial contraction of the stent, wherein the inside diameter of the contracted stent is greater than the original inside diameter of the polymeric tube.

17. The method according to claim 16, wherein the heated stent radially contracts at least partially due to heat shrinking of the polymer of the stent.

18. The method according to claim 16, wherein the heated stent is at a temperature from a glass transition temperature to a melting temperature of the polymer.

19. The method according to claim 16, wherein the heated stent is above ambient temperature.

20. A method for fabricating a medical assembly comprising:
    providing a polymeric tube fabricated from a polymer of an original inside diameter, wherein the polymer has a glass transition temperature;
    radially expanding the polymeric tube;
    fabricating a stent from the radially expanded polymeric tube;
    positioning the stent around a support element;
    heating the stent, wherein the heated stent is above ambient temperature and at a temperature from a glass transition temperature to a melting temperature of the polymer; and
    allowing the heated stent to radially contract onto the support element, wherein the heated stent radially contracts at least partially due to heat shrinking of the polymer of the stent, and wherein the inside diameter of the contracted stent is greater than the original inside diameter of the polymeric tube.

* * * * *